United States Patent
Maat et al.

(10) Patent No.: US 10,035,740 B2
(45) Date of Patent: Jul. 31, 2018

(54) MULTI-STAGE OXIDATIVE DEHYDROGENATION PROCESS WITH INTER-STAGE COOLING

(71) Applicant: TPC Group LLC, Houston, TX (US)

(72) Inventors: Clifford Alan Maat, Pearland, TX (US); Joseph G. Duff, League City, TX (US); Liana Caciula, Houston, TX (US); Michael O. Nutt, Pearland, TX (US); Robert Z. Confair, Friendswood, TX (US); Mark P. Kaminsky, Friendswood, TX (US); Jillian M. Horn, Houston, TX (US); Gus K. Georgeton, Friendswood, TX (US)

(73) Assignee: TPC Group LLC, Houston, TX (US)

( * ) Notice: Subject to any disclaimer, the term of this patent is extended or adjusted under 35 U.S.C. 154(b) by 230 days.

(21) Appl. No.: 14/771,302

(22) PCT Filed: Mar. 7, 2014

(86) PCT No.: PCT/US2014/021523
§ 371 (c)(1),
(2) Date: Aug. 28, 2015

(87) PCT Pub. No.: WO2014/138520
PCT Pub. Date: Sep. 12, 2014

(65) Prior Publication Data
US 2016/0023963 A1 Jan. 28, 2016

Related U.S. Application Data

(60) Provisional application No. 61/774,309, filed on Mar. 7, 2013, provisional application No. 61/844,490, filed on
(Continued)

(51) Int. Cl.
*C07C 5/327* (2006.01)
*C07C 2/26* (2006.01)
(Continued)

(52) U.S. Cl.
CPC .................. *C07C 5/48* (2013.01); *B01J 8/025* (2013.01); *B01J 8/04* (2013.01); *B01J 8/0419* (2013.01);
(Continued)

(58) Field of Classification Search
CPC .................................. C07C 5/327; C07C 2/26
(Continued)

(56) References Cited

U.S. PATENT DOCUMENTS 3,207,810 A 9/1965 Bajars
3,728,415 A 4/1973 Arganbright
(Continued)

FOREIGN PATENT DOCUMENTS

JP 2011148720 A 8/2011

OTHER PUBLICATIONS

Seyed Hamed Mahdaviani et al., "Selective ethylene dimerization toward 1-butene by a new highly efficient catalyst system and determination of its optimum operating conditions in a Buchi reactor", International Journal of Chemical Engineering and Applications, Oct. 2010, pp. 276-281, vol. 1, No. 3.
(Continued)

*Primary Examiner* — Thuan D Dang
(74) *Attorney, Agent, or Firm* — Michael W. Ferrell (57) ABSTRACT

A method of oxidatively dehydrogenating a dehydrogenation reactant includes providing a first gaseous feed stream to a first adiabatic, catalytic reaction zone with less than a stoichiometric amount of oxygen and superheated steam, oxidatively dehydrogenating dehydrogenation reactant in said first adiabatic, catalytic reaction zone and subsequently cooling the effluent, adding additional oxygen and reacting the effluent stream in at least one subsequent adiabatic reaction zone. The dehydrogenation system enables higher conversion and yield per pass and in some cases greatly
(Continued)

reduces steam usage and energy costs. In a preferred integrated process, ethylene is converted to n-butene which is then oxidatively dehydrogenated to butadiene.

18 Claims, 5 Drawing Sheets

Related U.S. Application Data on Jul. 10, 2013, provisional application No. 61/774,370, filed on Mar. 7, 2013, provisional application No. 61/844,483, filed on Jul. 10, 2013.

(51) Int. Cl.
    *C07C 5/48* (2006.01)
    *B01J 8/04* (2006.01)
    *B01J 8/02* (2006.01)
    *B01J 23/78* (2006.01)
    *C07C 2/36* (2006.01)

(52) U.S. Cl.
    CPC .......... *B01J 8/0453* (2013.01); *B01J 8/0492* (2013.01); *B01J 8/0496* (2013.01); *B01J 23/78* (2013.01); *C07C 2/36* (2013.01); *B01J 2208/00176* (2013.01); *B01J 2208/00256* (2013.01); *B01J 2208/00274* (2013.01); *B01J 2208/00362* (2013.01); *C07C 2523/745* (2013.01); *C07C 2527/185* (2013.01); *C07C 2527/187* (2013.01); *C07C 2531/14* (2013.01); *C07C 2531/24* (2013.01); *Y02P 20/125* (2015.11)

(58) Field of Classification Search
    USPC ................ 585/616, 621, 633, 510, 324, 329
    See application file for complete search history.

(56) References Cited

U.S. PATENT DOCUMENTS

| | | |
|---|---|---|
| 3,911,042 A | 10/1975 | Belov et al. |
| 3,925,498 A | 12/1975 | Stadig |
| 3,953,370 A | 4/1976 | Miklas |
| 3,969,429 A | 7/1976 | Belov et al. |
| 4,069,272 A | 1/1978 | Hutson, Jr. |
| 4,083,844 A | 4/1978 | Gottschlich et al. |
| 4,644,088 A * | 2/1987 | McFarland ............ B01J 23/755 585/624 |
| 4,658,074 A | 4/1987 | Bajars et al. |
| 5,162,595 A | 11/1992 | Wu |
| 6,998,504 B1 | 2/2006 | Unverricht et al. |
| 7,034,195 B2 | 4/2006 | Schindler et al. |
| 7,488,857 B2 | 2/2009 | Johann et al. |
| 8,088,962 B2 | 1/2012 | Klanner et al. |
| 2011/0288308 A1 | 11/2011 | Grasset et al. |

OTHER PUBLICATIONS

L. Marshall Welch et al., "Butadiene via oxidative dehydrogenation", Hydrocarbon Processing, Nov. 1978, pp. 131-136.

* cited by examiner

FIG. 1
AIR FED PROCESS FOR OXIDATIVE DEHYDROGENATION

MULTI-STAGE OXIDATIVE DEHYDROGENATION PROCESS WITH INTER-STAGE COOLING

CLAIM FOR PRIORITY

This application is based on PCT Patent Application Serial No. PT/US2014/021523, filed Mar. 7, 2014. Application No. PCT/US2014/021523 was based upon United States Provisional Application No. 61/774,309 filed Mar. 7, 2013, entitled "Multi-Stage Oxidative Dehydrogenation Process with Inter-Stage Cooling", as well as U.S. Provisional Application No. 61/844,490, filed Jul. 10, 2013, entitled "Manufacture of Butadiene from Ethylene With Multi-Stage Oxidative Dehydrogenation Process". Application No. PCT/US2014/021523 was also based upon U.S. Provisional Application No. 61/774,370, filed Mar. 7, 2013, entitled "Oxidative Dehydrogenation Process With Hydrocarbon Moderator Gas and Reduced Nitrogen Feed" and U.S. Provisional Application No. 61/844,483, filed Jul. 10, 2013, entitled "Manufacture of Butadiene from Ethylene With Hydrocarbon Moderator Gas and Reduced Nitrogen Feed". The priorities of the foregoing applications are hereby claimed and their disclosures incorporated herein by reference.

TECHNICAL FIELD

The present invention relates to a process and apparatus for producing dehydrogenated products from dehydrogenation reactants such as 1,3 butadiene from n-butenes by oxidative dehydrogenation in the presence of oxygen with multi-stage reaction zones provided with inter-stage cooling. The method and apparatus are operated such that increased conversion and yield per pass are realized and/or reduced levels of steam are required in adiabatic reaction zones as compared with a single stage reactor system. In one preferred aspect, the invention relates to a process for producing 1,3 butadiene from ethylene by dimerizing ethylene to n-butene followed by oxidative dehydrogenation of the butane.

BACKGROUND

Oxidative dehydrogenation, particularly oxidative dehydrogenation of n-butenes to make 1,3 butadiene is known. Process details are discussed at some length in Welch et al., *Butadiene via oxidative dehydrogenation*, Hydrocarbon Processing, November 1978, pp. 131-136. A high ratio of superheated steam to hydrocarbon in the feed supplies the necessary heat and increases the per pass yields by reducing partial pressures. Steam also acts as a heat sink in an adiabatic reaction system to moderate temperature rise during the intensely exothermic reaction. U.S. Pat. No. 7,034,195, to Schindler et al., discusses a two stage oxydehydrogenation arrangement at Col. 10, lines 38-53, but does not address the temperature control. U.S. Pat. No. 8,088,962, to Klanner et al., mentions multi-zone reactors at Col. 17, lines 51-56 in connection with 2-zone multiple catalyst tube fixed bed reactors. See, also, U.S. Pat. No. 6,998,504, to Unverricht et al. which recites tube-bundle reactors.

Fixed bed, adiabatic reactors are preferred over tube-bundle reactors because of their simple construction, low capital costs and low operating and maintenance costs as well as well established operational know-how with these reactors. In a traditional version of the oxidative dehydrogenation process, a large flow of steam is used to control the exotherm, typically in a steam to n-butene molar ratio of 12:1 or more. The large amounts of steam employed require large amounts of energy for superheating and vaporization as discussed hereinafter.

N-butene raw material for making butadiene is oftentimes scarce and difficult to obtain at prices suitable for commercial manufacturing operations. It is known in the art to dimerize ethylene to butene and use the recovered butene for manufacturing butadiene. U.S. Pat. No. 3,728,415 to Arganbright discloses producing butenes by dimerizing ethylene with a catalyst including palladium oxide with molybdenum oxide or tungsten oxide and using the product for dehydrogenation to make butadiene.

Other references of interest include the following: U.S. Pat. Nos. 3,911,042 and 3,969,429 to Belov et al. which disclose titanium/aluminum catalyzed dimerization of ethylene and note the product is useful for making butadiene; U.S. Pat. No. 7,488,857 to Johann et al. which discloses coproduction of butadiene and butene-1 from butane; and United States Patent Application Publication No. US 2011/0288308 to Grasset et al. which discloses ethylene dimerization with titanium/aluminum catalyst.

It is proposed in Japanese Patent Publication 2011-148720 to manufacture butadiene from ethylene by way of dimerizing ethylene followed by oxidative dehydrogenation using specified catalysts to minimize impact of various impurities. The method proposed includes the following steps (I) and (II): a step (I) for producing n-butene essentially free of isobutene by dimerizing ethylene at a reaction temperature of 150 to 400° C. in the presence of a catalyst consisting of nickel, alumina, and silica having a nickel content of 0.0001 to 1 wt. %; and a step (II) for producing butadiene by performing an oxidative dehydrogenation reaction on the n-butene obtained in said step (I) with oxygen at a reaction temperature of 300 to 600° C. in the presence of a complex metal oxide comprising molybdenum and bismuth as essential ingredients.

Existing oxidative dehydrogenation processes can be relatively impurity-sensitive and energy intensive due to the large recirculation rates of steam and nitrogen employed; moreover, there is an ever-present need to increase conversions and yields, especially conversions and yields per pass.

SUMMARY OF INVENTION

There is provided in accordance with the invention an improved method of oxidatively dehydrogenating a dehydrogenation reactant in a plurality of successive oxidative dehydrogenation reaction zones provided with heat exchanger(s) between the oxidative dehydrogenation reaction zones. The inventive process enables reduced steam usage and reduces associated energy and equipment costs. Up to six (6) successive oxidative dehydrogenation reaction zones may be employed, advantageously three to four (3-4) successive oxidative dehydrogenation zones and, perhaps most preferably, two (2) successive oxidative dehydrogenation reaction zones. The system arrangement according to the invention enables one to increase conversion and yields per pass as compared with a single stage adiabatic system, increasing conversions by 10% and more in some cases while increasing yields by up to approximately 15%.

A preferred process in accordance with the invention utilizing two-stage oxidative dehydrogenation includes (a) providing a first gaseous feed stream to a first adiabatic, catalytic reaction zone at a first-stage inlet temperature, the feed stream including a dehydrogenation reactant, oxygen and superheated steam, wherein the molar ratio of superheated steam to dehydrogenation reactant is up to 20:1 in a system provided to increase conversions and yield per pass and from 0.5:1 to 7.5:1 in a system to designed for reduced steam usage. In the first reaction zone, the dehydrogenation reactant is (b) oxidatively dehydrogenated to provide a first-stage effluent stream enriched in a dehydrogenated product at a first-stage effluent temperature above said first-stage inlet temperature; the effluent product stream is then (c) cooled in a first heat transfer zone to a second-stage inlet temperature lower than said first-stage effluent temperature to provide a second gaseous feed stream comprising superheated steam and dehydrogenation reactant and dehydrogenated product. The second gaseous feed stream at said second-stage inlet temperature is (d) fed to a second adiabatic, catalytic reaction zone along with additional oxygen; where dehydrogenation reactant in the second gaseous feed stream is (e) oxidatively dehydrogenated to provide a second stage effluent stream further enriched in said dehydrogenated product at a second stage effluent temperature above said second-stage inlet temperature. The process further includes (f) recovering said dehydrogenated product.

A particularly preferred process uses butene feedstock to make butadiene.

In one embodiment, ethylene is dimerized to provide the butane feedstock.

Figure 2:
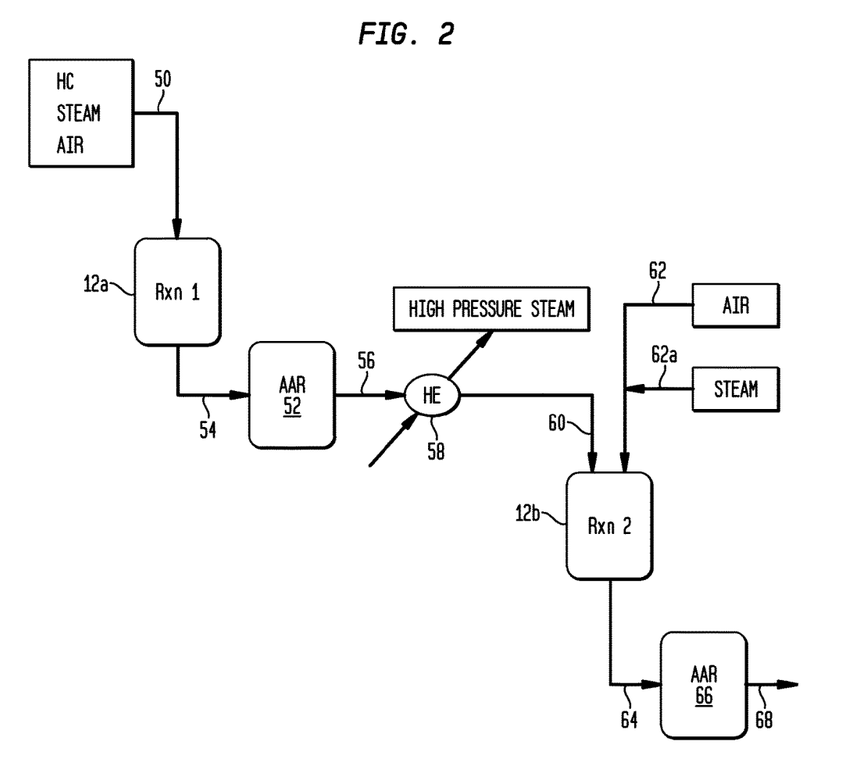
FIG. 2 is a schematic diagram illustrating a multi-stage reactor section with interstage cooling to which is used to practice oxidative dehydrogenation in accordance with the invention.

When adding interstage oxygen in a multi-stage oxidative dehydrogenation system, a fixed bed of acetylene and aldehyde removal catalyst (AAR) interposed between oxidative dehydrogenation zones can play an important safety role by combusting any unreacted oxygen leaving the first bed before supplemental oxygen is then added to the second bed. Without AAR catalyst available, there is potential to have too much oxygen transmitted from the first bed to the second bed, for example, due to an upset. If supplemental oxygen is added when there is too much spillover of oxygen from an upstream bed, one is vulnerable to exceeding the flammability limit for oxygen concentration as will be appreciated from FIG. 5, discussed hereinafter. Thus, a particularly preferred arrangement is to provide an AAR catalyst bed immediately downstream of each oxidative dehydrogenation reaction zone as is seen in FIG. 2, and discussed in connection with FIG. 3.

The multi-stage process can be further enhanced by oxygen and a moderator gas to replace some or all of the air in feed which reduces nitrogen recycle and improves heat recovery from overhead gasses.

Further details and advantages of the invention will be appreciated from the discussion which follows.

BRIEF DESCRIPTION OF DRAWINGS

The invention is described in detail below with reference to the drawings wherein like numerals designate similar parts and wherein.

DETAILED DESCRIPTION

The invention is described in detail below in connection with the Figures for purposes of illustration, only. The invention is defined in the appended claims. Terminology used throughout the specification and claims herein are given their ordinary meanings, unless a more specific definition appears herein.

%, percent and like terminology means weight percent unless otherwise specifically indicated.

In general, the process of this invention can be applied to the dehydrogenation of a wide variety of organic compounds suitable as dehydrogenation reactants. Such compounds normally will contain from 2 to 20 carbon atoms, at least one grouping, a boiling point below about 350° C., and may contain other elements, in addition to carbon and hydrogen, such as oxygen, halogens, nitrogen and sulfur. Preferred are compounds having 2 to 12 carbon atoms, and especially preferred, are compounds of 3 to 8 carbon atoms. Hydrocarbons of the above described carbon content form a preferred group.

Among the types of organic compounds which may be dehydrogenated by means of the process of this invention are nitriles, amines, alkyl halides, ethers, esters, aldehydes, ketones, alcohols, acids, alkyl aromatic compounds, alkyl heterocyclic compounds, alkenes, and the like. Illustration of dehydrogenation includes propionitrile to acrylonitrile; propionaldehyde to acrolein; ethyl chloride to vinyl chloride; methyl isobutyrate to methyl methacrylate; 2 or 3 chlorobutane-1 or 2,3-dichlorobutane to chloroprene; ethyl pyridine to vinyl pyridine; ethylbenzene to styrene; isopropylbenzene to alpha-methyl styrene; ethylchlorohexane to styrene; to styrene; cyclohexane to benzene; methylbutene to isoprene; cyclopentane to cyclopentene and cyclopentadiene-1,3; n-octane to ethyl benzene and ortho-xylene; monomethylheptanes to xylenes; ethyl acetate to vinyl acetate; 2,4,4-trimethylpentene to xylenes; and the like.

More typically, the invention is applied to the manufacture of butadiene by way of oxidatively dehydrogenating n-butenes.

Unless otherwise indicated, "butadiene" or "BD" refers to 1,3 butadiene or mixtures comprising 1,3 butadiene. Feedstocks include butene-1 as well as cis and trans 2-butene, which are sometimes referred to respectively as "C2B" and "T2B".

Ethylene dimerized to n-butene is one preferred raw material source for oxidative dehydrogenation according to the invention. Ethylene may be dimerized into n-butenes by a variety of catalytic processes. One suitable method is to utilize a homogeneous catalyst system which includes a nickel compound such as nickel phosphine oxide and an alkyl aluminum co-catalyst such as ethyl aluminum dichloride. Such processes produce predominantly 2-butenes. See, for example, U.S. Pat. No. 5,162,595 to Wu, the disclosure of which is incorporated by reference.

Alternatively, ethylene is dimerized into n-butenes suitable for use in connection with the present invention through the use of a homogeneous catalyst system which includes an organometallic titanium catalyst. In general, such processes include a titanium organometallic complex with at least one alkoxide ligand and an alkyl aluminum co-catalyst to produce predominantly 1-butene as is seen, for example, in United States Patent Application Publication No. US 2011/0288308 of Grasset et al., noted above, the disclosure of which is incorporated herein by reference. One suitable catalytic system includes titanium tetrabutoxide and triethyl aluminum. Titanium-based dimerization processes may be relatively selective, such as the Alphabutol® process and are reported to reduce fractionation costs when 1-butene of relatively high purity is required:

M = Metal
$L_n$ = Ligand

Another preferred source of raw material in some cases includes C4 Raffinate 2 and C4 Raffinate 3 streams. "Raffinate" refers to C4 streams wherein the butadiene has been removed by extraction as is well-known in the art. C4 Raffinate 2 refers to such streams where the isobutylene has also been removed, typically by reaction with methanol to make MTBE. C4 Raffinate 3 is produced from a C4 Raffinate 2 stream by removing the 1-butene. C4 Raffinate 2 and C4 Raffinate 3 are mixtures of butenes and butane as is seen in Table 1.

TABLE 1

Typical Compositions For C4 Raffinate 2 and C4 Raffinate 3 Streams, Per Cent by weight

| Components | C4 Raffinate 2 | C4 Raffinate 3 |
|---|---|---|
| Propylene | 0-1 | |
| Propadiene | 0-1 | |
| Isobutane | 1-7.5 | |
| Isobutylene (Isobutene) | 1-5 | |
| 1-Butene | 2.5-65 | 0.2 |
| 1,3-Butadiene | 0.1-0.5 | |
| Butane | 10-39 | 55.2 |
| Butene-2 (Isomer Mix) | 11-55 | 45.2 |

The hydrocarbon reactant butene(s) are added together with a hydrocarbon moderator gas, butane in such embodiments by using raffinate as feed.

"Adiabatic" and like terminology refers to reaction zones which retain heat of reaction and thus exhibit a temperature rise with respect to feed temperatures to the reaction zone. Preferably, the adiabatic reaction zones retain more than 75% of the heat of reaction generated therein and still more preferably over 90% of the heat of reaction generated therein.

"Indirect" heat transfer refers to heat transfer from one medium to another medium through a heat exchanger wall. When carrying out indirect heat exchange in connection with the inventive process, heat is transferred through a single heat exchanger wall from a higher temperature stream to a lower temperature stream, such as from reactor effluent to reactor feed in a feed or process stream superheater. Indirect heat transfer is carried out in accordance with the invention using tube and shell heat exchangers, plate and frame heat exchangers or other suitable equipment. Heat transfer or cooling may also be carried out in the heat exchange zones in connection with the invention by direct heat transfer, that is by atomizing a water spray into a reaction zone effluent in a heat transfer or cooling zone as described hereinafter.

"Moderator gas" and like terminology refers to gas which is substantially inert under conditions in the reactor, preferably undergoing conversion in the reactor of less than 10%; more preferably less than 5% and still more preferably less than 1% or 2%. Suitable moderator gasses generally include alkanes such as methane, ethane, propane, butane, pentane and hexane. A preferred moderator gas is natural gas which is predominately, typically more than 75% by volume, methane.

"Temperature delta" refers to a temperature difference, for example, the temperature difference between the input temperature of a stream provided to a heat exchange device and the output (exit) temperature of that stream from that heat exchange device. A temperature delta of a stream though a heat exchanger is thus the difference between the inlet temperature and outlet temperature of that stream.

Figure 1:
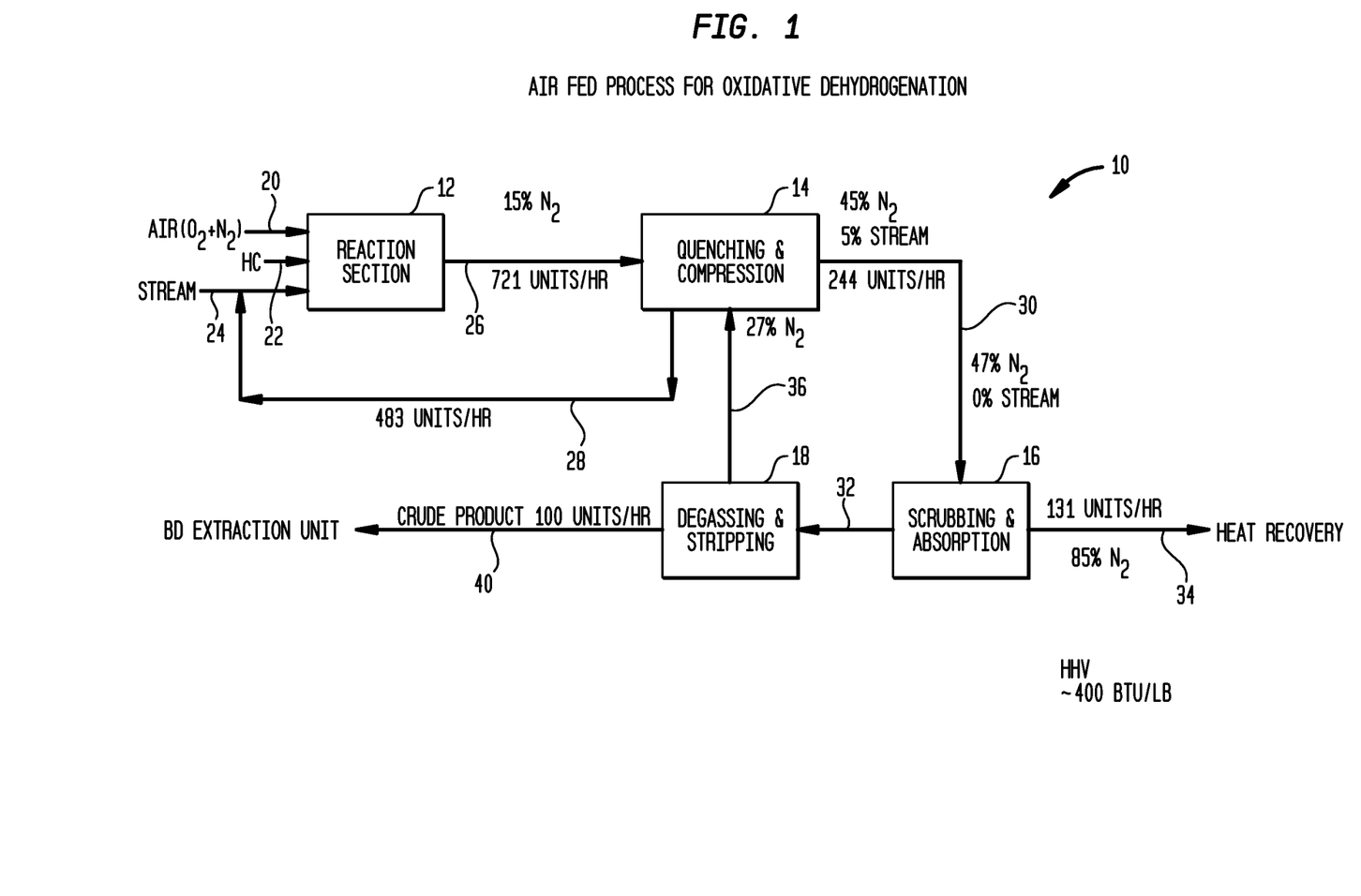
FIG. 1 is a schematic diagram illustrating operation of an oxidative dehydrogenation process to make butadiene with a conventional type reactor.

Referring to FIG. 1, there is shown schematically a conventional butadiene production system 10 of the class described herein for producing 100 units/hr of crude butadiene. "Units" refers to weight units in the discussion herein and on the Figures.

System 10 includes a reaction section 12 having a single reaction zone, quenching and compression sections indicated at 14, as well as scrubbing and absorption units indicated at 16 and degassing and stripping apparatus provided at 18.

In the process, air is fed to reaction section 12 along with n-butene and steam via lines 20, 22, 24. The effluent is forwarded to quenching and compression 14 via line 26 and most of the water is recycled to the reaction system via line 28. After quenching and compression an output stream 30 is forwarded to scrubbing and absorption 16. Butadiene product is absorbed in an absorbent tower at 16 and liquid effluent is passed via line 32 to degassing and stripping at 18, while overhead gas is provided to heat recovery via line 34.

From degassing and stripping at 18, off-gas is partially recycled via line 36 to quenching and compression at 14. The degassed fat absorber oil containing butadiene is fed forward via line 40 for extraction and further purification. Clean absorber oil is recycled to section 16.

Energy requirements per pound of butadiene produced for a conventional reaction section as shown in FIG. 1 can be summarized as in the following Table 2 for processes employing conventional steam/hydrocarbon molar ratios.

TABLE 2

Reaction Section Energy Utilization

| Total Energy required*: | 8890 BTU/LB BD |
|---|---|
| Energy for Superheating Feed | |

TABLE 2-continued

Reaction Section Energy Utilization

| | |
|---|---|
| Steam: | 1760 BTU/LB BD |
| Butene: | 150 BTU/LB BD |
| Energy for Vaporizing Butene | 310 BTU/LB BD |
| Energy for Vaporizing Steam | 6670 BTU/LB BD |

*Approx. values

It will be appreciated from Table 2 that approximately 95% of the energy required to operate the reaction section may be supplied by way of vaporizing or superheating steam in order bring the feed to temperature.

An oxidative dehydrogenation process for making butadiene of this invention (or other dehydrogenated product) includes providing a butene rich hydrocarbonaceous feed, vaporizing and superheating said hydrocarbonaceous butene rich feed, mixing said hydrocarbonaceous butene rich feed with superheated steam and an oxygen rich gas to form a reactor feed stream, hydrocarbonaceous butene rich feed and employing a reaction section with multiple reaction zones or stages and inter-stage cooling. Typically, a feed stream enters an adiabatic reaction zone at a temperature of 700° F. or so and exits that reaction zone at 1100° F. or so. Details as to feed compositions and operating temperatures appear in Welch et al., *Butadiene via oxidative dehydrogenation*, Hydrocarbon Processing, November 1978, pp. 131-136, the disclosure of which is incorporated herein by reference. Suitable catalysts are also described in Miklas, METHOD OF ACTIVATING ZINC-FERRITE OXIDATIVE DEHYDROGENATION CATALYST; U.S. Pat. No. 3,953,370; Apr. 27, 1976, as well as CATALYTIC OXIDATIVE DEHYDROGENATION PROCESS; U.S. Pat. No. 4,658,074, as well as U.S. Pat. No. 4,083,844 to Purdy, the disclosures of which are incorporated herein by reference. Acetylene removal catalysts (AAR catalysts) and their usage are described in pending Application No. PCT/US2011/000624, the disclosure of which is also incorporated by reference.

Figure 3:
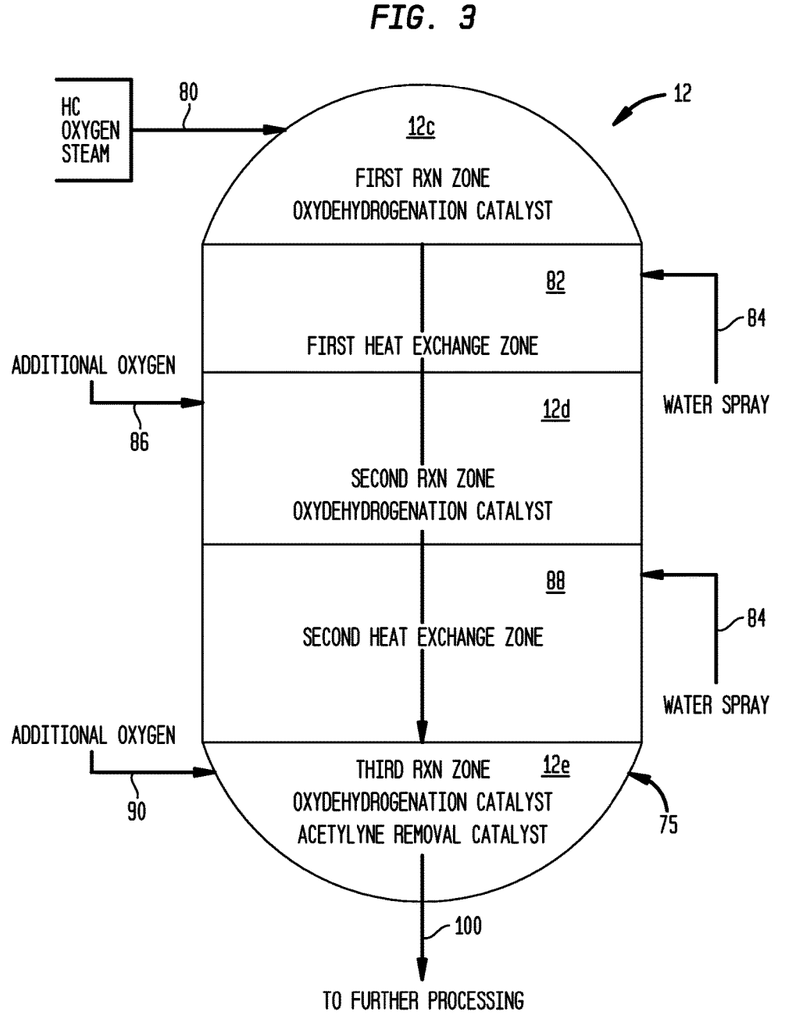
FIG. 3 is a schematic diagram illustrating another multi-stage reactor section with interstage cooling to which is used to practice oxidative dehydrogenation in accordance with the invention.

The method and apparatus of this invention is appreciated with reference to FIGS. 2 and 3, both of which are schematic diagrams of a reaction section 12 that can be used in connection with the other equipment shown in FIG. 1. In FIG. 2 hydrocarbon reactant is fed to a first adiabatic reactor along with steam via inlet 50 and less than a stoichiometric amount of oxygen, suitably ½ or so of a stoichiometric amount (i.e., 0.5 moles of oxygen for each mole of n-butene). In the first reactor 12a, a dehydrogenated product is produced by oxidative dehydrogenation and a temperature rise occurs. The effluent from reactor 12a is fed (without cooling) to a separate vessel 52 containing a fixed bed of acetylene and aldehyde removal catalyst (AAR line 54). The high temperature of the effluent is desirable in order to facilitate impurity removal by the catalyst. Suitable AAR catalysts and their usage are described in pending Application No. PCT/US2011/000624 noted above. After treatment in the first AAR zone 52, the effluent is passed via line 56 to a heat exchanger 58 to produce superheated steam, which can be used in the process. The cooled effluent, which contains superheated steam, unreacted hydrocarbon reactant, and dehydrogenated product is fed via line 60 to a second reactor 12b along with the balance of a stoichiometric amount of oxygen via line 62 to complete the reaction. If so desired, additional steam can be added via line 62a. The effluent from the second reactor is fed via line 64 (again, without cooling) to another vessel 66 containing a fixed bed of acetylene and aldehyde removal catalyst. A product stream 68 exiting the system can be processed by conventional means to recover and purify the product.

When feeding air or oxygen to a reaction zone, it is preferable to mix in steam or inerts in order to avoid the flammable regions of the reaction mixture as discussed hereinafter. To this end, steam or other inerts are mixed with oxygen or the oxygen source employed prior to injection into the reactor at one or all oxygen injection points.

In an alternate embodiment, the reaction and heat transfer zones may reside in a single vessel having the configuration shown in FIG. 3. In FIG. 3, there is shown a single vessel 75 reactor with multiple reaction zones 12c, 12d and 12e, each of which contains a ferrite oxydehydrogenation catalyst and, optionally, AAR catalyst, as noted above.

In FIG. 3, hydrocarbon reactant is fed to a first adiabatic reaction zone along with steam and less than a stoichiometric amount of oxygen, (i.e., 0.5 moles of oxygen for each mole of hydrocarbon reactant) suitably ⅓ or so of a stoichiometric amount. Feed is fed to first reaction zone 12c via line 80. In the first reaction zone, a dehydrogenated product is produced by oxidative dehydrogenation and a temperature rise occurs. The effluent is passed to a first heat exchange zone 82 where it is cooled either by indirect heat transfer, direct heat transfer or both. When direct heat transfer is used, water may be atomized into the heat exchange zone, as indicated at 84. A tube and shell heat exchanger may be used in heat transfer zone 82 to produce superheated steam or another heated process stream by indirect heat exchange as a separate stream, which can be used in the process either as superheated feed or to provide heat. The cooled effluent, which contains superheated steam, unreacted hydrocarbon reactant, and dehydrogenated product is fed to second reaction zone 12d along with another ⅓ of a stoichiometric amount of oxygen via line 86. The effluent is passed to a second heat exchange zone 88 where it is cooled and may be used to produce superheated steam as noted above. The cooled effluent, which contains superheated steam, unreacted hydrocarbon reactant, and dehydrogenated product is fed to a third reaction zone 12e along with another ⅓ of a stoichiometric amount of oxygen via line 90 to complete the reaction. The effluent from the third reaction zone indicated at 100 can be processed by conventional means to recover and purify the product.

Each of the oxidative dehydrogenation reaction zones is most preferably immediately above an AAR catalyst layer which removes impurities and acts to remove unwanted oxygen in case of an upset in the system as noted above. Positioning of the AAR catalyst layers is indicated in FIG. 3 in the third reaction zone, only; however it is appreciated that AAR layers are advantageously disposed below the oxidative dehydrogenation catalyst in the upper two reaction zones as well.

The arrangements shown in FIGS. 2, 3 and modes of operation enable employing steam:butene molar ratios of from 0.5:1 up to 7.5:1 in connection with adiabatic reaction zones so as to realize energy savings of up to 50% and more. The size of reactors, quench vessels and the size and complexity of heat recovery equipment can also be greatly reduced due to the smaller volume of gas that needs to be handled as seen in the following Table 3 which compare equipment requirements for a given production rate:

TABLE 3

Comparison of Equipment Requirements

| | | Single Stage Reactor | | Staged Reactors With Interstage Cooler (Stm:HC 6:1) | |
|---|---|---|---|---|---|
| Reactor | | Vessel ID | 14 ft | Vessel ID | 10 ft |
| | Interstage Cooler | — | | Exchanger Area | 1280 ft² |
| Downstream Heat Recovery | Downstream Heat Recovery Exchange 1 | Exchanger Area | 15360 ft² | Exchanger Area | 8460 ft² |
| | Downstream Heat Recovery Exchanger 2 | Exchanger Area | 5140 ft² | Exchanger Area | 3175 ft² |
| Quench Tower | | Tray Diameter | 21 ft | Tray Diameter | 16 ft |
| | | Packing Diameter | 19 ft | Packing Diameter | 14 ft |

Downstream heat exchanger area can be reduced by nearly 50% with similar levels of heat recovery.

Still further operating advantages can be realized by feeding oxygen moderator gas to replace all or some of the air feed to the process to reduce nitrogen levels in the system and improve heat recovery.

The inventive system may likewise be operated to increase conversions and yields per pass as compared with a single stage reactor, increasing conversions from 75-80% to over 85% and 95% under comparable conditions while increasing yields per pass from 70% to over 80%.

Figure 4:
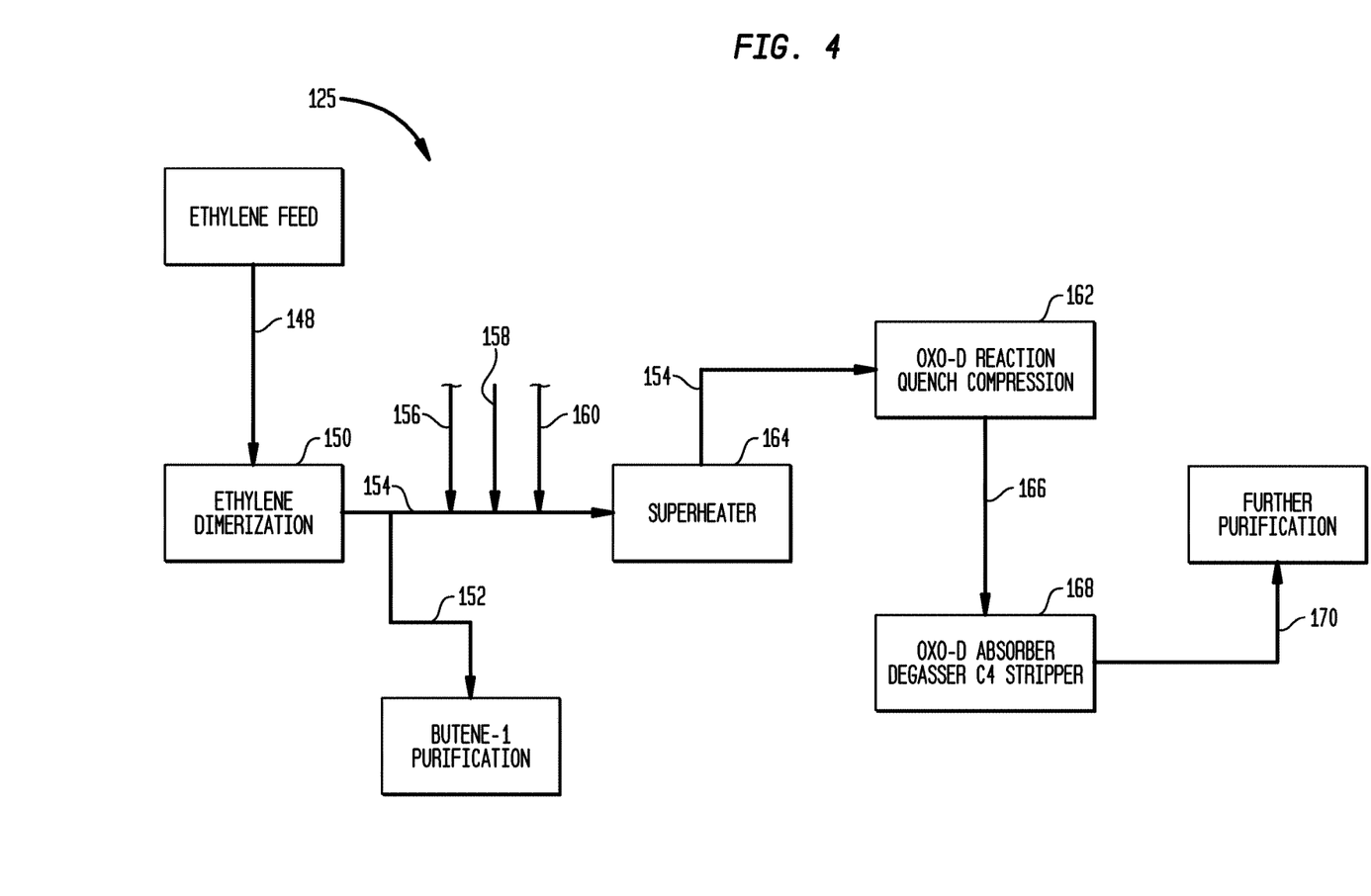
FIG. 4 is a flow diagram illustrating operation of an oxidative dehydrogenation process of the invention to make butene and butadiene based on ethylene as the raw material.

One preferred embodiment of the present invention is a co-production system 125 shown schematically in FIG. 4. Ethylene is provided to a homogeneous reactor 150 containing a titanium/aluminum homogeneous catalyst via line 148 wherein butene-1 is produced from the ethylene. The butene-1 is provided to a butene-rich product stream 152 as well as a butene-1 rich feed stream 154.

Stream 152 is purified and butene-1 (>99%) is recovered therefrom, while stream 154 is mixed with steam 156, a moderator gas 158 and an oxygen rich gas 160 and provided to an oxidative dehydrogenation unit as part of a reaction/quench/compression section 162 after superheating in a superheater 164. Section 162 may contain the reactor configuration shown in FIG. 2 or 3. Output 166 is enriched in butadiene and contains butene-1.

Stream 166 is fed to a product recovery system including an absorber, degasser and stripper units indicated at 168 and a crude butadiene stream 170 is recovered as described in connection with FIG. 1. Stream 170 is typically 50-60% by weight butadiene and is further purified by conventional means in order to provide butadiene of greater than 99% purity, while other C4's are recycled or otherwise recovered.

Figure 5:
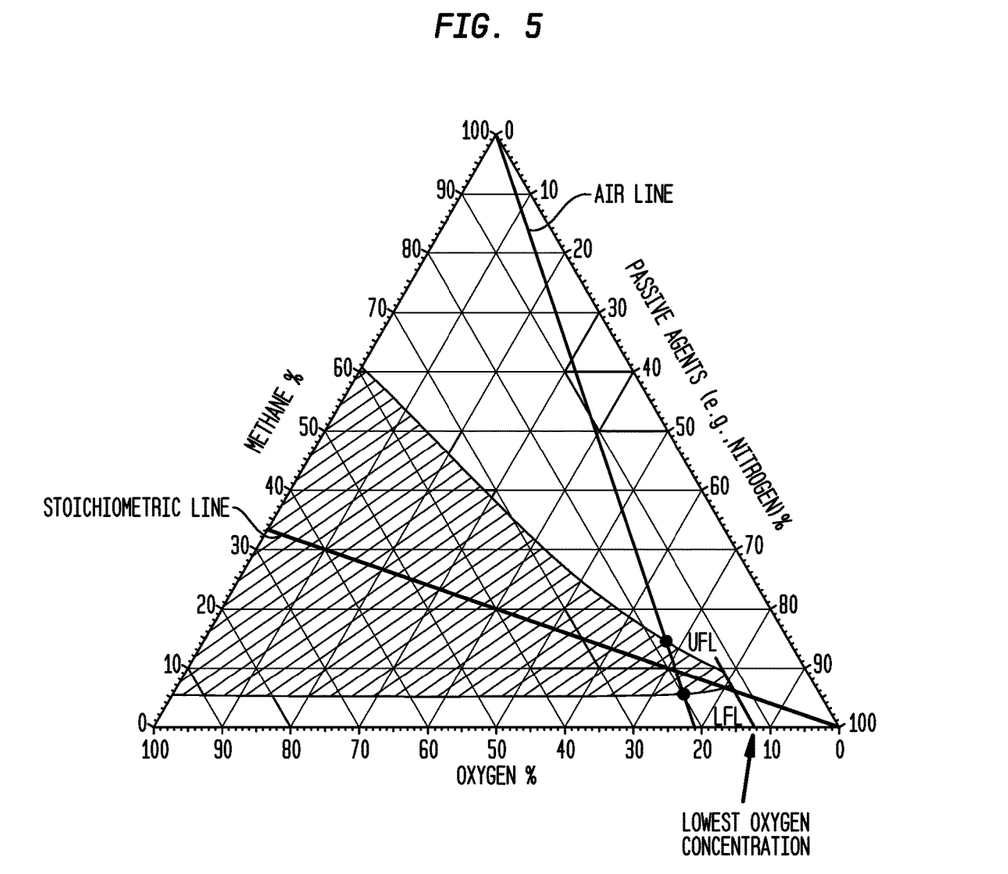
FIG. 5 is a ternary flammability diagram for methane/oxygen/inert gas mixtures sourced from http://cfbt-us.com/wordpress/?p=421. (2013 Attributed to GexCon).

Referring to FIG. 5, there is shown a ternary diagram illustrating the flammability region (shaded) of mixtures of methane/oxygen/and inerts such as nitrogen or steam on a mol % basis for a predetermined temperature and pressure. One of skill in the art will appreciate that the flammability region will vary depending on temperature, pressure, and composition of flammables/hydrocarbons in the reactor. It is seen in the diagram that at low levels of inerts especially, the flammability region for hydrocarbons is much expanded, as toward the left of the diagram. In operating the process of the present invention, it is much preferred to control the mixture composition, temperatures and pressures to operate outside of the flammability region of the reaction mixtures. A preferred method of operation is to add the oxygen to the steam and then mix the hydrocarbons. This avoids the "nose" of the flammability triangle and stays on the "fuel rich" side of the envelope.

For particular reaction compositions and conditions, flammability limits can be determined empirically or calculated from component data based on Le Chatelier's mixing rule, for example, for the lower flammability limit, LFL:

$$LFL_{Mix} = \frac{100}{C_1/LFL_1 + C_2/LFL_2 + \ldots + C_i/LFL_i}$$

There is thus provided in accordance with the present invention processes and apparatus for producing oxidative dehydrogenation in various aspects, including the embodiments of the invention enumerated below.

Embodiment No. 1 is a method of oxidatively dehydrogenating a dehydrogenation reactant comprising: (a) providing a first gaseous feed stream to a first adiabatic, catalytic reaction zone at a first-stage inlet temperature, the first feed stream including a dehydrogenation reactant, oxygen and superheated steam, wherein the molar ratio of superheated steam to dehydrogenation reactant is selected from one of the following ratios: from 0.5:1 to 20:1; 0.5:1 to 16:1; or from 0.5:1 to 12.5:1 or from 0.5:1 to 10:1 or from 0.5:1 to 7.5:1; (b) oxidatively dehydrogenating dehydrogenation reactant in said first adiabatic, catalytic reaction zone to provide a first-stage effluent stream enriched in said dehydrogenated product at a first-stage effluent temperature above said first-stage inlet temperature; (c) cooling the first-stage effluent stream in a first heat transfer zone to a second-stage inlet temperature lower than said first-stage effluent temperature to provide a second gaseous feed stream comprising superheated steam, dehydrogenation reactant and dehydrogenated product; (d) feeding said second gaseous feed stream at said second-stage inlet temperature to a second adiabatic, catalytic reaction zone along with additional oxygen; (e) oxidatively dehydrogenating dehydrogenation reactant in said second adiabatic, catalytic reaction zone to provide a second stage effluent stream further enriched in said dehydrogenated product at a second stage effluent temperature above said second-stage inlet temperature; and (f) recovering said dehydrogenated product.

Embodiment No. 2 is the method according to Embodiment No. 1, wherein the molar ratio of superheated steam to dehydrogenation reactant in said first gaseous feed stream is from 1:1 to 7.5:1.

Embodiment No. 3 is the method according to Embodiment No. 2, wherein the molar ratio of superheated steam to dehydrogenation reactant in said first gaseous feed stream is from 2:1 to 7:1.

Embodiment No. 4 is the method according to Embodiment No. 3, wherein the molar ratio of superheated steam to dehydrogenation reactant in said first gaseous feed stream is from 3:1 to 7:1.

Embodiment No. 5 is the method according to Embodiment No. 4, wherein the molar ratio of superheated steam to dehydrogenation reactant in said first gaseous feed stream is from 4:1 to 7:1.

Embodiment No. 6 is the method according to Embodiment No. 5, wherein the molar ratio of superheated steam to dehydrogenation reactant in said first gaseous feed stream is from 5:1 to 7:1.

Embodiment No. 7 is the method according to Embodiment No. 5, wherein the molar ratio of superheated steam to dehydrogenation reactant in said first gaseous feed stream is from 5:1 to 6.5:1.

Embodiment No. 8 is the method according to Embodiment No. 1, wherein the molar ratio of oxygen to dehydrogenation reactant in said first gaseous feed stream is from 0.1:1 to 0.85:1 or from 0.1:1 to 0.4:1.

Embodiment No. 9 is the method according to Embodiment No. 8, wherein the molar ratio of oxygen to dehydrogenation reactant in said first gaseous feed stream is from 0.2:1 to 0.4:1.

Embodiment No. 10 is the method according to Embodiment No. 9, wherein the molar ratio of oxygen to dehydrogenation reactant in said first gaseous feed stream is from 0.25:1 to 0.325:1.

Embodiment No. 11 is the method according to Embodiment No. 1, wherein additional oxygen is added to said second gaseous feed stream such that feed to the second adiabatic reaction zone has a molar ratio of oxygen:dehydrogenation reactant of from 0.1:1 to 0.85:1 or from 0.1:1 to 0.4:1.

Embodiment No. 12 is the method according to Embodiment No. 11, wherein additional oxygen is added to said second gaseous feed stream such that feed to the second adiabatic reaction zone has a molar ratio of oxygen:dehydrogenation reactant of from 0.2:1 to 0.4:1.

Embodiment No. 13 is the method according to Embodiment No. 12, wherein additional oxygen is added to said second gaseous feed stream such that feed to the second adiabatic reaction zone has a molar ratio of oxygen:dehydrogenation reactant of from 0.25:1 to 0.325:1.

Embodiment No. 14 is the method according to Embodiment No. 1, wherein the temperature delta between the first-stage inlet temperature and the first-stage effluent temperature is from 200° F. to 600° F.

Embodiment No. 15 is the method according to Embodiment No. 14, wherein the temperature delta between the first-stage inlet temperature and the first-stage effluent temperature is at least 250° F.

Embodiment No. 16 is the method according to Embodiment No. 15, wherein the temperature delta between the first-stage inlet temperature and the first-stage effluent temperature is at least 300° F.

Embodiment No. 17 is the method according to Embodiment No. 16, wherein the temperature delta between the first-stage inlet temperature and the first-stage effluent temperature is at least 350° F.

Embodiment No. 18 is the method according to Embodiment No. 1, wherein the temperature delta between the second stage inlet temperature and the second stage effluent temperature is from 200° F. to 600° F.

Embodiment No. 19 is the method according to Embodiment No. 18, wherein the temperature delta between the second stage inlet temperature and the second stage effluent temperature is at least 250° F.

Embodiment No. 20 is the method according to Embodiment No. 19, wherein the temperature delta between the second stage inlet temperature and the second stage effluent temperature is at least 300° F.

Embodiment No. 21 is the method according to Embodiment No. 20, wherein the temperature delta between the second stage inlet temperature and the second stage effluent temperature is at least 350° F.

Embodiment No. 22 is the method according to any one of Embodiment Nos. 1-21, wherein said dehydrogenation reactant comprises butenes and said dehydrogenated product comprises butadiene.

Embodiment No. 23 is the method according to Embodiment No. 22, wherein said butenes comprise one or more of 1-butene, C2B and T2B.

Embodiment No. 24 is the method according to Embodiment No. 23, wherein said butenes include C2B and T2B.

Embodiment No. 25 is the method according to any one of Embodiment Nos. 1-24, wherein said dehydrogenation reactant comprises butenes and said dehydrogenated product comprises butadiene and the first gaseous feed stream comprises butenes and butane.

Embodiment No. 26 is the method according to Embodiment No. 25, wherein said first gaseous feed stream comprises C4 Raffinate 2 or C4 Raffinate 3.

Embodiment No. 27 is the method according to any one of Embodiment Nos. 1-26, wherein said step of cooling said first stage effluent stream comprises indirect heat transfer.

Embodiment No. 28 is the method according to any one of Embodiment Nos. 1-27, wherein said step of cooling said first stage effluent stream comprises direct heat transfer.

Embodiment No. 29 is the method according to any one of Embodiment Nos. 1-28, wherein said step of cooling said first stage effluent stream comprises providing a water spray into said heat transfer zone.

Embodiment No. 30 is the method according to any of Embodiment Nos. 1-29, further comprising cooling the second-stage effluent stream and providing the cooled second-stage effluent stream along with additional oxygen to a third adiabatic reaction zone and dehydrogenating dehydrogenation reactant in said third adiabatic reaction zone.

Embodiment No. 31 is the method according to any of Embodiment Nos. 1-30, further comprising providing at least one of the reaction zones with an acetylene removal catalyst.

Embodiment No. 32 is the method according to Embodiment No. 31, wherein the acetylene removal catalyst comprises Ni, Fe, an alkali metal, and optionally an alkaline earth element.

Embodiment No. 33 is the method according to any of Embodiment Nos. 1-32, further comprising controlling the composition of reaction feed streams and reaction conditions to avoid flammable mixture regions in said reaction zones.

Embodiment No. 34 is the method according to any one of Embodiment Nos. 1-33 or 55-102, wherein at least one of the gaseous feed streams to a reactor comprises a moderator gas. Moderator gas may be present in such embodiments in relatively large amounts if so desired; for example, with moderator gas: reactant hydrocarbon molar ratios of anywhere from 0.5:1 to 15:1, if so desired, such that the moderator gas:oxygen molar ratios in the feed are quite high, up to about 50 or so. The moderator gas:oxygen molar ratio may be, for example, from 50:1 to 0.5:1; or from 20:1 to 0.5:1.

Embodiment No. 35 is the method of oxidatively dehydrogenating a dehydrogenation reactant according to Embodiment No. 34, wherein the molar ratio of hydrocarbon moderator gas to oxygen in said feed stream comprising a moderator gas is from 16:1 to 0.5:1.

Embodiment No. 36 is the method of oxidatively dehydrogenating a dehydrogenation reactant according to Embodiment No. 35, wherein the molar ratio of hydrocarbon moderator gas to oxygen in said feed stream comprising a moderator gas is from 8:1 to 1:1.

Embodiment No. 37 is the method of oxidatively dehydrogenating a dehydrogenation reactant according to Embodiment No. 35, wherein the molar ratio of hydrocarbon moderator gas to oxygen in said feed stream comprising a moderator gas is from 6:1 to 1.5:1.

Embodiment No. 38 is the method of oxidatively dehydrogenating a dehydrogenation reactant according to Embodiment No. 34, wherein said feed stream comprising a moderator gas comprises nitrogen and the molar ratio of oxygen:nitrogen in the feed stream containing moderator gas is at least 0.5.

Embodiment No. 39 is the method of oxidatively dehydrogenating a dehydrogenation reactant according to Embodiment No. 34, wherein said feed stream comprising a moderator gas comprises nitrogen and the molar ratio of oxygen:nitrogen in the feed stream containing moderator gas is at least 2.

Embodiment No. 40 is the method of oxidatively dehydrogenating a dehydrogenation reactant according to Embodiment No. 34, wherein said feed stream comprising a moderator gas comprises nitrogen and the molar ratio of oxygen:nitrogen in the feed stream containing moderator gas is at least 10.

Embodiment No. 41 is the method of oxidatively dehydrogenating a dehydrogenation reactant according to Embodiment No. 34, wherein said feed stream comprising a moderator gas comprises nitrogen and the molar ratio of oxygen:nitrogen in the feed stream containing moderator gas is at least 20.

Embodiment No. 42 is the method according to Embodiment No. 34, wherein said moderator gas comprises an alkane.

Embodiment No. 43 is the method according to Embodiment No. 34, wherein said moderator gas comprises methane, ethane, propane, butane, pentane or hexane.

Embodiment No. 44 is the method according to Embodiment No. 34, wherein said moderator gas comprises methane.

Embodiment No. 45 is an apparatus for oxidatively dehydrogenating a dehydrogenation reactant comprising: (a) a first adiabatic reaction zone having a fixed bed of ferrite dehydrogenation catalyst adapted for receiving a gaseous feed stream comprising a dehydrogenation reactant, oxygen and superheated steam and providing an effluent stream enriched in dehydrogenated product at an effluent temperature higher than the temperature of the feed stream to the first adiabatic reaction zone; (b) a heat exchanger for receiving said effluent stream and cooling said effluent stream to a temperature lower than said effluent temperature to provide a second gaseous feed stream; (c) a second adiabatic reaction zone having a fixed bed of ferrite dehydrogenation catalyst adapted for receiving said second gaseous feed stream; and (d) an oxygen feed for supplying additional oxygen to said second reaction zone.

Embodiment No. 46 is the apparatus according to Embodiment No. 45, further comprising: (e) a second heat exchanger for receiving a second effluent stream at a second effluent temperature and cooling said second effluent stream to a temperature lower than said second effluent temperature to provide a third gaseous feed stream; (f) a third adiabatic reaction zone having a fixed bed of ferrite dehydrogenation catalyst adapted for receiving said third gaseous feed stream; and (g) an oxygen feed for supplying additional oxygen to said third reaction zone.

Embodiment No. 47 is the apparatus according to Embodiment Nos. 45 or 46, wherein the reaction zones and heat exchangers are housed within a single vessel.

Embodiment No. 48 is the apparatus according to Embodiment No. 45, 46 or 47, wherein the dehydrogenation catalysts in said first and second adiabatic reaction zones are the same catalyst.

Embodiment No. 49 is the apparatus according to Embodiment Nos. 45, 46, 47 or 48, wherein the dehydrogenation catalyst consists essentially of: oxygen, a major proportion of iron; a minor proportion of zinc; and smaller amounts of manganese; phosphorus, with the residue of a nitrate free calcium precursor.

Embodiment No. 50 is the apparatus according to Embodiment Nos. 45, 46, 47, 48 or 49, wherein at least one of said heat exchangers comprises a tube and shell heat exchanger.

Embodiment No. 51 is the apparatus according to Embodiment Nos. 45, 46, 47, 48 or 49, wherein at least one of said heat exchangers comprises a direct heat exchanger.

Embodiment No. 52 is the apparatus according to Embodiment No. 51, wherein said direct heat exchanger includes a water spray into said reactor effluent stream.

Embodiment No. 53 is the apparatus according to Embodiment No. 52, wherein said water spray provides atomized spray into said reactor effluent stream Embodiment No. 54 is the apparatus for oxidatively dehydrogenating a dehydrogenation reactant comprising: (a) one or more upstream adiabatic reaction zone(s) having a fixed bed of ferrite dehydrogenation catalyst adapted for receiving gaseous feed comprising a dehydrogenation reactant, oxygen and superheated steam and providing an effluent stream enriched in dehydrogenated product at an effluent temperature higher than the temperature of the gaseous feed to the adiabatic reaction zone; (b) one or more heat exchanger(s) for receiving effluent stream(s) from said adiabatic reaction zone(s) and cooling said effluent stream(s) to a temperature lower than said effluent temperature to provide a gaseous feed stream(s) to other adiabatic reaction zone(s) at a lower temperature; (c) a downstream adiabatic reaction zone having a fixed bed of ferrite dehydrogenation catalyst atop a fixed bed of acetylene removal catalyst adapted for receiving a gaseous feed stream; and (d) oxygen feed for supplying oxygen to said reaction zone(s).

Embodiment No. 55 is the improvement in a method of making butadiene by way of oxidative dehydrogenation, comprising: (a) dimerizing ethylene to n-butene in a homogeneous catalytic reaction medium to provide an n-butene rich stream; (b) mixing the n-butene rich stream with steam and an oxygen rich gas to provide a gaseous feed stream; (c) providing the gaseous feed stream to a plurality of adiabatic, catalytic reaction zones arranged in series, the feed stream including n-butene, oxygen and superheated steam, wherein the molar ratio of superheated steam to n-butene is selected from one of the following ratios: 0.5:1 to 20:1; 0.5:1 to 16:1; from 0.5:1 to 12.5:1 or from 0.5:1 to 10:1 or from 0.5:1 to 7.5:1; (d) oxidatively dehydrogenating n-butene reactant in said plurality of adiabatic, catalytic reaction zones to provide a plurality of effluent streams enriched in butadiene as compared with the gaseous feed stream; (e) cooling the effluent stream(s) in one or more heat transfer zones to a temperature lower than its effluent temperature and injecting additional oxygen into the effluent stream(s) prior to feeding the effluent stream to a subsequent oxidative dehydrogenation reaction zone; and (f) recovering said butadiene.

Embodiment No. 56 is the improvement according to Embodiment No. 55, utilizing from 2 to 6 oxidative dehydrogenation zones arranged in series.

Embodiment No. 57 is the improvement according to Embodiment No. 55, utilizing at least 3 oxidative dehydrogenation zones arranged in series.

Embodiment No. 58 is the improvement according to Embodiment No. 55, utilizing at least 4 oxidative dehydrogenation zones arranged in series.

Embodiment No. 59 is the improvement according to Embodiment No. 55, wherein the molar ratio of superheated steam to n-butene in said gaseous feed stream is from 1:1 to 7.5:1.

Embodiment No. 60 is the improvement according to Embodiment No. 56, wherein the molar ratio of superheated steam to n-butene in said gaseous feed stream is from 2:1 to 7:1.

Embodiment No. 61 is the improvement according to Embodiment No. 60, wherein the molar ratio of superheated steam to n-butene in said gaseous feed stream is from 3:1 to 7:1.

Embodiment No. 62 is the improvement according to Embodiment No. 61, wherein the molar ratio of superheated steam to n-butene in said gaseous feed stream is from 4:1 to 7:1.

Embodiment No. 63 is the improvement according to Embodiment No. 62, wherein the molar ratio of superheated steam to n-butene in said gaseous feed stream is from 5:1 to 7:1.

Embodiment No. 64 is the improvement according to Embodiment No. 63, wherein the molar ratio of superheated steam to n-butene in said gaseous feed stream is from 5:1 to 6.5:1.

Embodiment No. 65 is the improvement according to Embodiment No. 55, wherein the molar ratio of oxygen to n-butene in said gaseous feed stream is from 0.1:1 to 0.4:1.

Embodiment No. 66 is the improvement according to Embodiment No. 65, wherein the molar ratio of oxygen to n-butene in said gaseous feed stream is from 0.2:1 to 0.4:1.

Embodiment No. 67 is the improvement according to Embodiment No. 66, wherein the molar ratio of oxygen to n-butene in said gaseous feed stream is from 0.25:1 to 0.325:1.

Embodiment No. 68 is the improvement in a method of co-producing butene-1 and butadiene from ethylene, comprising: (a) providing ethylene to a homogeneous reaction medium including a homogeneous titanium/aluminum catalyst housed in a dimerization reactor; (b) dimerizing ethylene predominantly to butene-1 in the homogeneous reaction medium to provide (i) a butene-1 rich feed and (ii) a butene-1 rich product stream; (c) withdrawing and purifying the butene-1 rich product stream and recovering butene-1 therefrom; (d) mixing said hydrocarbonaceous butene-1 rich feed stream with steam and oxygen to provide a gaseous feed stream; (e) providing the gaseous feed stream to a plurality of adiabatic, catalytic reaction zones arranged in series, the feed stream including n-butene, oxygen and superheated steam, wherein the molar ratio of superheated steam to n-butene is selected from one of the following ratios: 0.5:1 to 20:1; 0.5:1 to 16:1; from 0.5:1 to 12.5:1 or from 0.5:1 to 10:1 or from 0.5:1 to 7.5:1; (f) oxidatively dehydrogenating n-butene reactant in said plurality of adiabatic, catalytic reaction zones to provide a plurality of effluent streams enriched in butadiene as compared with the gaseous feed stream; (g) cooling the effluent stream(s) in one or more heat transfer zones to a temperature lower than its effluent temperature and injecting additional oxygen into the effluent stream(s) prior to feeding the effluent stream to a subsequent oxidative dehydrogenation reaction zone; and (h) recovering said butadiene.

Embodiment No. 69 is the improvement according to any of Embodiment Nos. 55-68, wherein the effluent is treated with AAR catalyst prior to feeding the effluent to another oxidative dehydrogenation zone.

Embodiment No. 70 is the improvement according to any of Embodiment Nos. 55-69, wherein the effluent from each oxidative dehydrogenation zone is treated with AAR catalyst.

Embodiment No. 71 is an apparatus adapted for practicing the improvements according to Embodiment Nos. 55-70.

Embodiment No. 72 is a method of making butadiene comprising: (a) dimerizing ethylene to n-butene in a homogeneous catalytic reaction medium to provide an n-butene rich stream; (b) mixing the n-butene rich stream with steam and an oxygen rich gas to provide a first gaseous feed stream; (c) providing the first gaseous feed stream to a first adiabatic, catalytic reaction zone at a first-stage inlet temperature, the feed stream including a n-butene, oxygen and superheated steam, wherein the molar ratio of superheated steam to n-butene is selected from one of the following ratios: 0.5:1 to 16:1; from 0.5:1 to 12.5:1 or from 0.5:1 to 10:1 or from 0.5:1 to 7.5:1; (d) oxidatively dehydrogenating n-butene in said first adiabatic, catalytic reaction zone to provide a first-stage effluent stream enriched in butadiene at a first-stage effluent temperature above said first-stage inlet temperature; (e) cooling the first-stage effluent stream in a first heat transfer zone to a second-stage inlet temperature lower than said first-stage effluent temperature to provide a second gaseous feed stream comprising superheated steam, n-butene and butadiene; (f) feeding said second gaseous feed stream at said second-stage inlet temperature to a second adiabatic, catalytic reaction zone along with additional oxygen; (g) oxidatively dehydrogenating n-butene in said second adiabatic, catalytic reaction zone to provide a second stage effluent stream further enriched in said butadiene at a second stage effluent temperature above said second-stage inlet temperature; and (h) recovering said butadiene.

Embodiment No. 73 is the method according to Embodiment No. 72, wherein the molar ratio of superheated steam to n-butene in said first gaseous feed stream is from 1:1 to 7.5:1.

Embodiment No. 74 is the method according to Embodiment No. 73, wherein the molar ratio of superheated steam to n-butene in said first gaseous feed stream is from 2:1 to 7:1.

Embodiment No. 75 is the method according to Embodiment No. 74, wherein the molar ratio of superheated steam to n-butene in said first gaseous feed stream is from 3:1 to 7:1.

Embodiment No. 76 is the method according to Embodiment No. 75, wherein the molar ratio of superheated steam to n-butene in said first gaseous feed stream is from 4:1 to 7:1.

Embodiment No. 77 is the method according to Embodiment No. 76, wherein the molar ratio of superheated steam to n-butene in said first gaseous feed stream is from 5:1 to 7:1.

Embodiment No. 78 is the method according to Embodiment No. 76, wherein the molar ratio of superheated steam to n-butene in said first gaseous feed stream is from 5:1 to 6.5:1.

Embodiment No. 79 is the method according to Embodiment No. 72, wherein the molar ratio of oxygen to n-butene in said first gaseous feed stream is from 0.1:1 to 0.4:1.

Embodiment No. 80 is the method according to Embodiment No. 79, wherein the molar ratio of oxygen to n-butene in said first gaseous feed stream is from 0.2:1 to 0.4:1.

Embodiment No. 81 is the method according to Embodiment No. 80, wherein the molar ratio of oxygen to n-butene in said first gaseous feed stream is from 0.25:1 to 0.325:1.

Embodiment No. 82 is the method according to Embodiment No. 72, wherein additional oxygen is added to said second gaseous feed stream such that feed to the second adiabatic reaction zone has a molar ratio of oxygen:n-butene of from 0.1:1 to 0.4:1.

Embodiment No. 83 is the method according to Embodiment No. 82, wherein additional oxygen is added to said second gaseous feed stream such that feed to the second adiabatic reaction zone has a molar ratio of oxygen:n-butene of from 0.2:1 to 0.4:1.

Embodiment No. 84 is the method according to Embodiment No. 83, wherein additional oxygen is added to said second gaseous feed stream such that feed to the second adiabatic reaction zone has a molar ratio of oxygen:n-butene of from 0.25:1 to 0.325:1.

Embodiment No. 85 is the method according to any one of Embodiment Nos. 72-102, wherein said step of cooling said first stage effluent stream comprises indirect heat transfer.

Embodiment No. 86 is the method according to any one of Embodiment Nos. 72-102, wherein said step of cooling said first stage effluent stream comprises direct heat transfer.

Embodiment No. 87 is the method according to any one of Embodiment Nos. 72-102, wherein said step of cooling said first stage effluent stream comprises providing a water spray into said heat transfer zone.

Embodiment No. 88 is the method according to any of Embodiment Nos. 72-102, further comprising cooling the second-stage effluent stream and providing the cooled second-stage effluent stream along with additional oxygen to a third adiabatic reaction zone and dehydrogenating n-butene in said third adiabatic reaction zone.

Embodiment No. 89 is the method according to any of Embodiment Nos. 72-102, further comprising providing at least one of the reaction zones with an acetylene removal catalyst.

Embodiment No. 90 is the method according to Embodiment No. 89, wherein the acetylene removal catalyst comprises Ni, Fe, an alkali metal, and optionally an alkaline earth element.

Embodiment No. 91 is the method according to any of Embodiment Nos. 72-102, further comprising controlling the composition of reaction feed streams and reaction conditions to avoid flammable mixture regions in said reaction zones.

Embodiment No. 92 is the method according to any of Embodiment Nos. 72-102, wherein the homogeneous reaction medium in the dimerization reactor comprises a homogeneous catalyst comprising a nickel compound and an alkyl aluminum co-catalyst.

Embodiment No. 93 is the method according to Embodiment No. 92, wherein the homogeneous catalyst comprises a nickel phosphine oxide and ethyl aluminum dichloride.

Embodiment No. 94 is the method according to Embodiment No. 92, wherein the n-butene in the oxidative dehydrogenation gaseous feed streams is predominantly 2-butenes.

Embodiment No. 95 is the method according to any of Embodiment Nos. 72-91, wherein the homogeneous reaction medium in the dimerization reactor comprises a homogeneous titanium/aluminum catalyst.

Embodiment No. 96 is the method according to Embodiment No. 95, wherein the homogeneous titanium/aluminum catalyst comprises a titanium organometallic complex with at least one alkoxide ligand and an alkyl aluminum co-catalyst.

Embodiment No. 97 is the method according to Embodiment No. 96, wherein the homogeneous titanium/aluminum catalyst comprises titanium tetrabutoxide and triethyl aluminum.

Embodiment No. 98 is the method according to Embodiment No. 95, wherein the butene in the oxidative dehydrogenation gaseous feed streams is predominantly 1-butene.

Embodiment No. 99 is the method of co-producing butene-1 and butadiene from an ethylene raw material feed comprising: (a) providing ethylene to a homogeneous reaction medium including a homogeneous titanium/aluminum catalyst housed in a dimerization reactor; (b) dimerizing ethylene predominantly to butene-1 in the homogeneous reaction medium to provide (i) a butene-1 rich feed and (ii) a butene-1 rich product stream; (c) withdrawing and purifying the butene-1 rich product stream and recovering butene-1 therefrom; (d) mixing said hydrocarbonaceous butene-1 rich feed stream with steam and oxygen to provide a first gaseous feed stream; (e) providing the first gaseous feed stream to a first adiabatic, catalytic reaction zone at a first-stage inlet temperature, the feed stream including a n-butene, oxygen and superheated steam, wherein the molar ratio of superheated steam to n-butene is from 0.5:1 to 7.5:1; (f) oxidatively dehydrogenating dehydrogenation reactant in said first adiabatic, catalytic reaction zone to provide a first-stage effluent stream enriched in said dehydrogenated product at a first-stage effluent temperature above said first-stage inlet temperature; (g) cooling the first-stage effluent stream in a first heat transfer zone to a second-stage inlet temperature lower than said first-stage effluent temperature to provide a second gaseous feed stream comprising superheated steam, n-butene and butadiene; (h) feeding said second gaseous feed stream at said second-stage inlet temperature to a second adiabatic, catalytic reaction zone along with additional oxygen; (i) oxidatively dehydrogenating n-butene in said second adiabatic, catalytic reaction zone to provide a second stage effluent stream further enriched in said butadiene at a second stage effluent temperature above said second-stage inlet temperature; and (j) recovering said butadiene.

Embodiment No. 100 is the method according to Embodiment No. 99, wherein the homogeneous titanium/aluminum catalyst comprises a titanium organometallic complex with at least one alkoxide ligand and an alkyl aluminum co-catalyst.

Embodiment No. 101 is the method according to Embodiment No. 100, wherein the homogeneous titanium/aluminum catalyst comprises titanium tetrabutoxide and triethyl aluminum.

Embodiment No. 102 is the method according to any of Embodiment Nos. 1-101, wherein said butadiene enriched product stream is treated with an AAR catalyst bed.

Embodiment No. 103 is an apparatus for oxidatively dehydrogenating an n-butene comprising: (a) a homogeneous catalytic reactor adapted to produce n-butene from ethylene; (b) steam and oxygen feed adapted to mix steam and oxygen with n-butene produced in said catalytic reactor to provide a gaseous feed stream comprising n-butene, superheated steam and oxygen; (c) a first adiabatic reaction zone having a fixed bed of ferrite dehydrogenation catalyst adapted for receiving the gaseous feed stream comprising n-butene derived from ethylene, oxygen and superheated steam and providing an effluent stream enriched in butadiene at an effluent temperature higher than the temperature of the feed stream to the first adiabatic reaction zone; (d) a heat exchanger for receiving said effluent stream and cooling said effluent stream to a temperature lower than said effluent temperature to provide a second gaseous feed stream; (e) a second adiabatic reaction zone having a fixed bed of ferrite dehydrogenation catalyst adapted for receiving said second gaseous feed stream; and (f) an oxygen feed for supplying additional oxygen to said second reaction zone.

Embodiment No. 104 is an apparatus according to Embodiment No. 103, further comprising: (g) a second heat exchanger for receiving a second effluent stream at a second effluent temperature and cooling said second effluent stream to a temperature lower than said second effluent temperature to provide a third gaseous feed stream; (h) a third adiabatic reaction zone having a fixed bed of ferrite dehydrogenation catalyst adapted for receiving said third gaseous feed stream; and (i) an oxygen feed for supplying additional oxygen to said third reaction zone.

Embodiment No. 105 is the apparatus according to Embodiment Nos. 103 or 104, wherein the reaction zones and heat exchangers are housed within a single vessel.

Embodiment No. 106 is the apparatus according to Embodiment Nos. 103, 104 or 105, wherein the oxidative dehydrogenation catalysts in said first and second adiabatic reaction zones are the same catalyst.

Embodiment No. 107 is the apparatus according to Embodiment Nos. 103, 104, 105 or 106, wherein at least one of said heat exchangers comprises a tube and shell heat exchanger.

Embodiment No. 108 is the apparatus according to Embodiment Nos. 103, 104, 105 or 106, wherein at least one of said heat exchangers comprises a direct heat exchanger.

Embodiment No. 109 is the apparatus according to Embodiment No. 108, wherein said direct heat exchanger includes a water spray into said reactor effluent stream.

Embodiment No. 110 is the apparatus according to claim 109, wherein said water spray provides atomized spray into said reactor effluent stream.

When moderator gas is used in place of steam, which may be in connection with any of the foregoing embodiments, moderator gas:reactant hydrocarbon molar ratios of anywhere from 3 to 12 are typical, with moderator gas:oxygen molar ratios of from 8:1 to 45:1 being typical. Following are exemplary ratios which may be used with or without air in the feed and with or without purified oxygen in the feed in connection with any of the foregoing embodiments:

TABLE 4

Steam Replacement Molar Ratios

| Steam to HC | Methane to HC | Methane to Oxygen |
|---|---|---|
| 3 | 12 | 41.9 |
| 5 | 10 | 34.9 |
| 7 | 8 | 27.9 |
| 9 | 6 | 20.9 |
| 12 | 3 | 10.48 |

Moderator gas:oxygen molar ratios of from 10:1 to 30:1 are preferred in some cases.

While the invention has been described in detail, modifications within the spirit and scope of the invention will be readily apparent to those of skill in the art. In view of the foregoing discussion, relevant knowledge in the art and references, including co-pending applications, discussed above in connection with the Background and Detailed Description, the disclosures of which are all incorporated herein by reference, further description is deemed unnecessary. In addition, it should be understood that aspects of the invention and portions of various embodiments may be combined or interchanged either in whole or in part. Furthermore, those of ordinary skill in the art will appreciate that the foregoing description is by way of example only, and is not intended to limit the invention.

What is claimed is:

1. A method of oxidatively dehydrogenating a dehydrogenation reactant comprising:
   (a) providing a first gaseous feed stream to a first adiabatic, catalytic reaction zone at a first-stage inlet temperature, the first feed stream including a dehydrogenation reactant, oxygen and superheated steam, wherein the molar ratio of superheated steam to dehydrogenation reactant is from 0.5:1 to 7.5:1;
   (b) oxidatively dehydrogenating dehydrogenation reactant in said first adiabatic, catalytic reaction zone to provide a first-stage effluent stream enriched in said dehydrogenated product at a first-stage effluent temperature above said first-stage inlet temperature;
   (c) cooling the first-stage effluent stream in a first heat transfer zone to a second-stage inlet temperature lower than said first-stage effluent temperature to provide a second gaseous feed stream comprising superheated steam, dehydrogenation reactant and dehydrogenated product, wherein the cooling of the first stage effluent stream is carried out (i) by indirect heat exchange with a heat exchanger or (ii) by direct heat exchange by way of atomizing water into said stream;
   (d) feeding said second gaseous feed stream at said second-stage inlet temperature to a second adiabatic, catalytic reaction zone along with additional oxygen;
   (e) oxidatively dehydrogenating dehydrogenation reactant in said second adiabatic, catalytic reaction zone to provide a second stage effluent stream further enriched in said dehydrogenated product at a second stage effluent temperature above said second-stage inlet temperature; and
   (f) recovering said dehydrogenated product,
   wherein the temperature delta between the first stage inlet temperature and the first stage effluent temperature is from 200° F. to 600° F. and the temperature delta between the second stage inlet temperature and the second stage effluent temperature is from 200° F. to 600° F.

2. The method according to claim 1, wherein the molar ratio of superheated steam to dehydrogenation reactant in said first gaseous feed stream is from 3:1 to 7:1.

3. The method according to claim 1, wherein the molar ratio of oxygen to dehydrogenation reactant in said first gaseous feed stream is from 0.1:1 to 0.85:1.

4. The method according to claim 1, wherein the molar ratio of oxygen to dehydrogenation reactant in said first gaseous feed stream is from 0.1:1 to 0.4:1.

5. The method according to claim 1, wherein additional oxygen is added to said second gaseous feed stream such that feed to the second adiabatic reaction zone has a molar ratio of oxygen:dehydrogenation reactant of from 0.1:1 to 0.85:1.

6. The method according to claim 1, wherein additional oxygen is added to said second gaseous feed stream such that feed to the second adiabatic reaction zone has a molar ratio of oxygen:dehydrogenation reactant of from 0.1:1 to 0.4:1.

7. The method according to claim 1, wherein the temperature delta between the first-stage inlet temperature and the first-stage effluent temperature is at least 250° F.

8. The method according to claim 1, wherein the temperature delta between the second stage inlet temperature and the second stage effluent temperature is at least 250° F.

9. The method according claim 1, wherein said dehydrogenation reactant comprises butenes and said dehydrogenated product comprises butadiene.

10. The method according to claim 1, wherein said step of cooling said first stage effluent stream comprises indirect heat transfer.

11. The method according to claim 1, wherein said step of cooling said first stage effluent stream comprises direct heat transfer utilizing a tube and shell heat exchanger or a plate and frame heat exchanger.

12. The method according to claim 1, wherein said step of cooling said first stage effluent stream comprises providing a water spray into said heat transfer zone.

13. The method according to claim 1, further comprising cooling the second-stage effluent stream and providing the cooled second-stage effluent stream along with additional oxygen to a third adiabatic reaction zone and dehydrogenating dehydrogenation reactant in said third adiabatic reaction zone.

14. The method according to claim 1, further comprising providing at least one of the reaction zones with an acetylene removal catalyst.

15. The method according to claim 14, wherein the acetylene removal catalyst comprises Ni, Fe, an alkali metal, and optionally an alkaline earth element.

16. The method according to claim 1, carried out in an apparatus for oxidatively dehydrogenating a dehydrogenation reactant comprising:
(a) a first adiabatic reaction zone having a fixed bed of ferrite dehydrogenation catalyst adapted for receiving a gaseous feed stream comprising a dehydrogenation reactant, oxygen and superheated steam and providing an effluent stream enriched in dehydrogenated product at an effluent temperature higher than the temperature of the feed stream to the first adiabatic reaction zone;
(b) a heat exchanger for receiving said effluent stream and cooling said effluent stream to a temperature lower than said effluent temperature to provide a second gaseous feed stream;
(c) a second adiabatic reaction zone having a fixed bed of ferrite dehydrogenation catalyst adapted for receiving said second gaseous feed stream; and
(d) an oxygen feed for supplying additional oxygen to said second reaction zone,
wherein a bed of acetylene and aldehyde removal catalyst is interposed between said first and second adiabatic reaction zones.

17. The method according to claim 1, carried out in an apparatus for oxidatively dehydrogenating a dehydrogenation reactant comprising:
(a) a first adiabatic reaction zone having a fixed bed of ferrite dehydrogenation catalyst adapted for receiving a gaseous feed stream comprising a dehydrogenation reactant, oxygen and superheated steam and providing an effluent stream enriched in dehydrogenated product at an effluent temperature higher than the temperature of the feed stream to the first adiabatic reaction zone;
(b) a heat exchanger for receiving said effluent stream and cooling said effluent stream to a temperature lower than said effluent temperature to provide a second gaseous feed stream;
(c) a second adiabatic reaction zone having a fixed bed of ferrite dehydrogenation catalyst adapted for receiving said second gaseous feed stream; and
(d) an oxygen feed for supplying additional oxygen to said second reaction zone,
wherein a bed of acetylene and aldehyde removal catalyst is provided immediately downstream of each adiabatic reaction zone.

18. In a method of making butadiene by way of oxidative dehydrogenation, the improvement comprising:
(a) dimerizing ethylene to n-butene in a homogeneous catalytic reaction medium to provide an n-butene rich stream;
(b) mixing the n-butene rich stream with steam and an oxygen rich gas to provide a gaseous feed stream;
(c) providing the gaseous feed stream to a plurality of adiabatic, catalytic reaction zones arranged in series, the feed stream including n-butene, oxygen and superheated steam, wherein the molar ratio of superheated steam to n-butene is from 0.5:1 to 7.5:1;
(d) oxidatively dehydrogenating n-butene reactant in said plurality of adiabatic, catalytic reaction zones to provide a plurality of effluent streams enriched in butadiene as compared with the gaseous feed stream;
(e) cooling the effluent stream(s) in one or more heat transfer zones to a temperature lower than its effluent temperature, wherein the cooling of an effluent stream is carried out (i) by indirect heat exchange with a heat exchanger or (ii) by direct heat exchange by way of atomizing water into said stream and injecting additional oxygen into the effluent stream(s) prior to feeding the effluent stream to a subsequent oxidative dehydrogenation reaction zone; and
(f) recovering said butadiene,
wherein the temperature delta between a first stage inlet temperature and a first stage effluent temperature is from 200° to 600° F. and the temperature delta between a second stage inlet temperature and a second stage effluent temperature is from 200° to 600° F.

* * * * *